United States Patent [19]

Sitrin et al.

[11] Patent Number: 4,667,024

[45] Date of Patent: May 19, 1987

[54] PROCESS FOR THE PREPARATION OF PURIFIED VANCOMYCIN CLASS ANTIBIOTICS

[75] Inventors: Robert D. Sitrin, Plymouth Meeting; Kenneth M. Snader, Hatboro; Gail F. Wasserman, Devon, all of Pa.

[73] Assignee: SmithKline Beckman Corporation, Philadelphia, Pa.

[21] Appl. No.: 513,511

[22] Filed: Jul. 13, 1983

[51] Int. Cl.$^4$ .................. C07H 1/00; C07C 103/52
[52] U.S. Cl. .................. 536/16.9; 536/18.5; 536/127; 530/412; 530/417
[58] Field of Search .............. 536/16.8, 16.9, 128, 536/18.5, 127, 22

[56] References Cited

U.S. PATENT DOCUMENTS

| | | | |
|---|---|---|---|
| 3,928,571 | 12/1975 | Raum | 424/118 |
| 3,952,095 | 4/1976 | Hamill et al. | 424/118 |
| 3,985,690 | 10/1976 | Duncan et al. | 536/22 |
| 4,083,964 | 4/1978 | Michel et al. | 424/118 |
| 4,169,141 | 9/1979 | Topliss et al. | 536/16.8 |
| 4,171,412 | 10/1979 | Coupek et al. | 525/329 |
| 4,378,348 | 3/1983 | Nishida et al. | 424/118 |
| 4,416,994 | 11/1983 | Nakatsukasa et al. | 435/253 |
| 4,440,753 | 4/1984 | McCormic et al. | 424/124 |
| 4,461,723 | 7/1984 | Hershberger et al. | 260/112.5 R |
| 4,468,462 | 8/1984 | Malin et al. | 435/253 |
| 4,491,660 | 1/1985 | Gendrich et al. | 536/22 |

OTHER PUBLICATIONS

Cuatrecasas, "Journal of Biological Chemistry", vol. 245, No. 12, pp. 3059-3065, 1970.
DePedro et al., "FEMS Microbiology Letters", 9(1980), pp. 215-217.
Cuatrecasas, "Biochemistry", vol. 11, No. 12, pp. 2291-2298, 1972.
Perkins et al., "Annals of the New York Academy of Sciences", vol. 235, pp. 348-363, 1974.
Bio-Rad Bulletin 1085, 1982.
Williams et al., "Topics in Antibiotic Chemistry", 5, pp. 119-158; 1980.
Nieto et al., Biochemical Journal, 123, pp. 789-803, 1971.

*Primary Examiner*—Johnnie R. Brown
*Attorney, Agent, or Firm*—Edward T. Lentz; Janice E. Williams; Alan D. Lourie

[57] ABSTRACT

A novel process for the isolation and purification of vancomycin class antibiotics which utilized affinity chromatography by the formation of a sorption complex between the antibiotic and an immobilizing ligand selected from -D-alanyl-D-alanine or -X-D-alanyl-D-alanine, wherein X is an amino acid radical and the novel affinity chromatography sorbent employed therein are disclosed.

19 Claims, No Drawings

PROCESS FOR THE PREPARATION OF PURIFIED VANCOMYCIN CLASS ANTIBIOTICS

BACKGROUND OF THE INVENTION

The vancomycin class of antibiotics has been described as crystalline, amphoteric, strongly levo-rotatory antibiotics of relatively high molecular weight [Williams et al., Topics in Antibiotic Chemistry, 5, pp 119-158 (1980)]. The vancomycin class of antibiotics also exhibits a reversal of inhibition when synthetic peptides terminating in D-alanyl-D-alanine were introduced to whole cell and cell free preparations [Nieto et al. Biochemical Journal, 26, 139 (1972)]. The known members of this class consist of vancomycin, ristocetin, actinoidin, avoparcin, actaplanin, teichomycin $A_2$, LL-AM-374, A 477, OA 7653 and A 35512B as well as the individual factor antibiotics thereof. A novel vancomycin class antibiotic, designated AAD 216 complex and its individual factor antibiotics, AAD 216A, AAD 216B and AAD 216C, are disclosed and claimed in U.S. Pat. No. 4,548,974, filed concurrently herewith. Isolation and purification of these vancomycin antibiotics entail standard procedures known in the art. The present invention relates to specific affinity chromatography for facile isolation and purification of the vancomycin class of antibiotics.

Affinity chromatography involves the following general steps: (1) contacting an impure solution of the compound to be isolated with a solid carrier matrix to which an immobilizing ligand, capable of forming a sorption complex with said compound, has been attached; (2) forming the sorption complex; (3) removing the impurities and then (4) dissociating the sorption complex in order to isolate the compound in a purified state. Specifically, murein precursors, UDP-muramyl-pentapeptide has been purified utilizing affinity column chromatography on vancomycin-Sepharose [DePedro et al., FEMS Microbiology Letters, 9, pp 215-217 (1980)].

SUMMARY OF THE INVENTION

The present invention relates to a novel process for the isolation and purification of vancomycin class antibiotics utilizing affinity chromatography by the formation of a sorption complex between the vancomycin class antibiotic to be isolated and an immobilizing ligand selected from -D-alanyl-D-alanine or -X-D-alanyl-D-alanine wherein X is an amino acid radical. Another aspect of this invention relates to the specific affinity chromatography sorbent employed in tne claimed process. The affinity chromatography sorbent comprises a solid support matrix to which an immobilizing ligand selected from -D-alanyl-D-alanine or X-D-alanyl-D-alanine, wherein X is defined above, has been attached.

DETAILED DESCRIPTION OF THE INVENTION

The novel affinity chromatography process of this invention relates to a method for the preparation of purified vancomycin class antibiotics which comprises: (1) the contacting of an impure solution containing the antibiotic to be purified with a solid carrier matrix to which immobilized ligands selected from -D-alanyl-D-alanine and -X-D-alanyl-D-alanine, wherein X is an amino acid radical, has been attached; (2) thereby, forming a sorption complex between the antibiotic and the immobilizing ligand; (3) removing the impurities from the solid carrier matrix and the sorption complex attached thereto, and (4) dissociating the sorption complex to isolate and recover the purified antibiotic.

The vancomycin class of antibiotics consists of vancomycin, ristocetin, actinoidin, avoparcin, actaplanin, teichomycin $A_2$, LL-AM-374, A 477, OA-7653, A 35512B and AAD 216 complex as well as the individual factors of said antibiotics. Specifically, vancomycin, ristocetin, avoparcin, teichomycin $A_2$, A 35512B and the AAD 216 complex are purified employing the process of this invention.

The isolation and purification of the vancomycin class antibiotics utilizing this novel affinity chromatography process is accomplished from any impure solution of the antibiotic to be isolated. Particularly, the desired antibiotics can be isolated and purified directly from a fermentation broth which results from the cultivation of producing microorganisms under conditions known to the art. Further, the fermentation broth may be subject to known preliminary isolation techniques prior to the affinity chromatography process of this invention. Such preliminary isolation techniques include, without limitation, filtration, extraction, precipitation, non-affinity chromatography and the like. The process of this invention may also be employed to remove impurities which do not form a sorption complex with the immobilizing ligands and that are difficult to remove from the antibiotic under known purification procedures. Such difficult impurities include by-products of the standard fermentation process which coincidentally have the same high pressure liquid chromatography retention time as the desired antibiotic.

The isolation and purification of the vancomycin class antibiotics utilizing this novel affinity chromatography process includes the step of dissociating the sorption complex between the antibiotic and the immobilizing ligand. The dissociation of the sorption complex can be accomplished employing a basic buffer solution in the presence of a polar organic solvent. Illustrative of the basic buffer solutions which can be utilized are known basic buffer solutions such as, 0.4M sodium bicarbonate at pH 9.5; 0.5M triethylammonium carbonate at pH 9; 0.25M sodium bicarbonate at pH 9; and 0.25M sodium bicarbonate at pH 9.5. Illustrative of the polar organic solvent which can be employed is acetonitrile.

Another aspect of the present invention is the novel sorbent which comprises a solid carrier matrix to which an immobilizing ligand selected from -D-alanyl-D-alanine or -X-D-alanyl-D-alanine, wherein X is an amino acid radical, has been attached.

Illustrative of the solid carrier matricies which may be employed in this invention are the known categories of affinity chromatography supports, such as, agarose, dextran, cellulose, polystyrene, polyacrylamide, silica controlled pore glass, nylon, acrylic copolymers and polyesters. Particular supports suitable for the claimed sorbent are agarose, Sepharose (a beaded form of agarose) and acrylic copolymers. These affinity chromatography supports may contain a "spacer arm", which is a neutral or charged radical of a specific length to which the immobilizing ligand is attached. A spacer arm interposed between the matrix and ligand in some cases facilitates effective binding. Specifically, Affi-Gel® 10 [BIO-RAD Laboratories], which is a N-hydroxysuccinimide ester of a derivatized crosslinked agarose gel bead containing a neutral 10-atom spacer arm, has been utilized in the present sorbent.

Illustrative of the immobilizing ligand, -X-D-alanyl-D-alanine, are tripeptides wherein X is an amino acid radical. Such tripeptides include α-N-acetyl-L-lysyl-D-alanyl-D-alanine, ε-N-acetyl-L-lysyl-D-alanyl-D-alanine, glycyl-D-alanyl-D-alanine, L-alanyl-D-alanyl-D-alanine, L-ornithyl-D-alanyl-D-alanine, L-tryrosyl-D-alanyl-D-alanine and D-alanyl-D-alanyl-D-alanine. Specifically, α-N-acetyl-L-lysyl-D-alanyl-D-alanine was employed as an immobilizing ligand in the present invention. Additionally, the dipeptide, D-alanyl-D-alanine has been employed as an immobilizing ligand.

The preparation of the sorbent utilized in the process of the present invention involves a coupling reaction between the immobilizing ligand and the solid carrier matrix. The procedures for coupling amino acids to solid carrier matricies are described in Cuatrecasas et al., Biochemistry, Vol. 11, No. 12, pp 2291-2298 (1972) and U.S. Pat. No. 4,171,412.

The following examples are illustrative of the process for preparing the sorbent of the present invention and the process for the preparation of purified vancomycin class antibiotics and therefore are not to be considered limiting the present invention as described in the claims appended hereto.

EXAMPLE 1

Tripeptide Affinity Chromatography Sorbent

Within a twenty minute time period, Affi-Gel ® 10 (75 μmoles) was suspended in isopropanol (5 ml), filtered and washed with distilled water (3×5 ml) at 4° C. The gel was added to a tripeptide solution, α-N-acetyl-L-lysyl-D-alanyl-D-alanine (55 mg) in 5 ml. 0.1M sodium bicarbonate −0.5M sodium chloride at pH 8.5. The resultant suspension was nutated, shaken with a circular motion, for 4 hours at 4° C. and then centrifuged for 10 minutes at 4° C. The liquid fraction was decanted and the solid fraction resuspended in 5 ml 0.1M sodium bicarbonate - 0.5M sodium chloride at pH 8.5. Ethanolamine hydrochloride (0.5 ml–1M) at pH 8 was added and the mixture nutated for 1 hour at 4° C. the mixture was transferred to a 0.7×10 cm column and washed alternately with 0.05 M TRIS–0.5M sodium chloride pH 8; 0.05M sodium formate–and 0.5M sodium chloride pH 4 (5×5 ml of each solution). The column containing the desired sorbent was stored at 4° C. in 10 mM sodium phosphate–0.02 percent sodium azide at pH 7.0 until needed.

EXAMPLE 2

Dipeptide Affinity Chromatography Sorbent

Within a 10 minute time period Affi-Gel ® 10 (5 g) was suspended in isopropanol (20 ml) and washed with distilled water (3×20 ml) at 4° C. The gel was added to a dipeptide solution, D-alanyl-D-alanine (5.28 mg) in 10 ml 0.1M sodium bicarbonate- 0.5 M sodium chloride at pH 8.5. The resultant suspension was nutated for 1 hour at ambient temperature and then filtered. The solid fraction was treated with ethanolamine (6 ml–1M) at pH 9 and the mixture nutated for 1 hour at room temperature. The ethanolamine was then filtered off and the gel washed alternately with 0.05 M TRIS hydrochloride–0.5M sodium chloride pH 8; 0.05M sodium formate–0.5M sodium chloride pH 4 (5×30 ml of each solution and 30 ml water between each washing). The resultant sorbent was equilibrated in 20 mM sodium phosphate, pH 7 and 0.02 percent sodium azide and stored at 4° C. until needed.

EXAMPLE 3

Affinity Chromatography of Vancomycin Fermentation Broth

A sorbent prepared according to the procedure of Example 2 (2 ml) was equilibrated with 20 mM sodium phosphate at pH 7 and added to a clarified fermentation broth of Streptomyces orientalis NRRL 2452 (8.5 ml which contained 8.07 mg of vancomycin) which had been neutralized with 0.01N hydrochloric acid. The mixture was nutated for 30 minutes at ambient temperature and then transferred to a 1.5×15 cm column. The gel containing the sorption complex of vancomycin and the immobilized ligand, -D-alanyl-D-alanine was washed with 20 mM sodium phosphate (20 ml) at pH 7. The sorption complex was dissociated and the vancomycin eluted with 30 percent acetonitrile in 0.4M sodium bicarbonate (2 column volumes) at pH 9.5. The appropriate fractions determined by U.V. absorbance at 280 nm and activity against B. subtilis, were combined and lyophilized to afford 5.46 mg. of purified vancomycin by analytical high pressure liquid chromatography analysis.

Similarly, the tripeptide affinity chromatography sorbent, prepared according to Example 1, is utilized in the above described procedure to purify vancomycin from a clarified fermentation broth.

EXAMPLE 4

Affinity Chromatography of AAD 216 Complex Fermentation Broth

A sorbent prepared according to the procedure of Example 2 (2 ml) was equilibrated with 20 mM sodium phosphate at pH 7 and added to a clarified fermentation broth of Kibdelosporangium aridum Shearer, gen. nov., sp. nov, ATCC 39323, as described in U.S. Pat. No. 4,548,974, (9.0 ml) which was neutralized using 0.25N hydrochloric acid. The mixture was nutated for 30 minutes at ambient temperature and then transferred to a 1.5×15 cm column. The gel containing the sorption complex of AAD 216 complex and the immobilizing ligand, -D-alanyl-D-alanine, was washed with 20 mM sodium phosphate (20 ml) at pH 7. The column was eluted with (1) 0.4M ammonium acetate (15 ml) at pH 7.8; (2) 10 percent aqueous acetonitrile (15 ml); and (3) 30 percent acetonitrile–0.5M triethylammonium bicarbonate at pH 9 until no further change in U.V. absorbance at 280 nm. The fractions from the 10 percent aqueous acetonitrile were combined and lyophilized to afford the purified AAD 216 complex (2.04 mg. containing 0.83 mg AAD 216A, 0.58 mg AAD 216B and 0.63 mg AAD 216C).

Similarly, the tripeptide affinity chromatography sorbent, prepared according to Example 1, is utilized in the above described procedure to purify AAD 216 complex from a clarified fermentation broth.

EXAMPLE 5

Sorption Complex Formation and Dissociation Batch Assays

Four samples (0.5 ml) of a sorbent prepared according to the procedure of Example 2 were individually washed with 20 mM sodium phosphate (2×3 ml) at pH 7 in assay tubes. Ristocetin (2.7 μmoles) in 20 mM sodium phosphate (3 ml) at pH 7 was introduced into each tube and the mixtures nutated for 30 minutes at ambient temperature. Each of the mixtures was centrifuged for 10 minutes and the supernatant decanted. Each sample was washed with 20 mM sodium phosphate (4×3 ml). The amount of ristocetin in the sorption complex formed in tubes 1 to 4 was 2.26, 2.34, 2.60 and 2.58 μmoles, respectively. The following elution buffer solutions were utilized to dissociate the respective sorption complexes in tubes 1 to 4: (1) 30 percent acetonitrile–0.25M sodium bicarbonate (3 ml) at pH 9; (2) 20 percent acetonitrile–0.25 M sodium bicarbonate (3 ml) at pH 9; (3) 20 percent acetonitrile–0.25M sodium bicarbonate (3 ml) at pH 9.5; and (4) 0.5M ammonium bicarbonate (3 ml) pH 7.8. After each tube was nutated for 30 minutes at ambient temperature and then centrifuged for 10 minutes. Each tube was then washed with the appropriate elution buffer solution (4×3 ml) and respective the supernatant and the washes combined. The amount of ristocetin recovered from each tube was as follows: 1.65 μmoles (73%), 1.79 μmoles (76%), 1.87 μmoles (73%) and 0.2 μmoles (7.6%) respectively. The amounts of ristocetin were determined by U.V. absorbance at 282 nm.

EXAMPLE 6

Following the batch assay procedure of Example 5, AAD 216 complex (3.1 mg) was applied to the sorbent. The amount of AAD 216 complex in the sorption complex was 2.5 mg. The amount of AAD 216 recovered after elution with 30 percent acetonitrile −0.25M sodium bicarbonate at pH 9 was 2.1 mg.

EXAMPLES 7–12

Sorption Complex Formation and Dissociation Column Assay

A 0.7×13 cm column containing 0.5 ml of affinity chromatography sorbent prepared according to the procedure of Example 2 was washed with 20 mM sodium phosphate (5 ml) at pH 7. Onto the column was loaded the antibiotic solution to be assayed. (See table below for initial amounts). The column was then was washed with 20 mM sodium phosphate (2×100 μl) and let stand at ambient temperature for 30 minutes. The column was washed with additional 20 mM sodium phosphate (4 ml). The amount of unbound antibiotic was calculated by high pressure liquid chromatography and/or U.V. absorbance at 280 nm of the washes. The column was eluted with various elution buffer solutions (5 ml) with 0.5 ml solution on the column for 15 minutes at ambient temperature (see table below). The eluant was lyophized and then quantitated.

| Initial Antibiotic (mg) | Amount Bound (mg) | Amount Recovered (mg) |
|---|---|---|
| $^A$Vancomycin (0.063) | 0.063 | 0.053 |
| $^A$Vancomycin (2.1) | 2.1 | 2.1 |
| $^A$Avoparcin (0.076) | 0.076 | 0.050 |
| $^B$Ristocetin (2.1) | 2.1 | 1.8 |
| $^B$A 35512B (1.4) | 1.4 | 1.2 |
| $^B$Teichomycin A$_2$ (1.0) | 1.0 | 0.62 |

$^A$30 percent acetonitrile in 0.5 M triethylammonium bicarbonate pH 9
$^B$30 percent acetonitrile in 0.4 M sodium bicarbonate pH 9.5

EXAMPLE 13

Following the column assay procedure of Examples 7–12 but utilizing the affinity chromatography sorbent prepared according to Example 1 containing the immobilizing ligand -α-N-L-lysyl-D-alanyl-D-alanine, vancomycin (2.64 moles) was loaded onto the column. The amount of vancomycin bound was 2.43 μmoles. After elution with 30 percent of acetonitrile–0.4M sodium bicarbonate (4 column volumes) at pH 9.5, the amount of vancomycin recovered was 2.23 μmoles.

What is claimed is:

1. An affinity chromatography process for the preparation of a purified vancomycin class antibiotic which comprises: (1) contacting an impure solution containing the antibiotic with a solid carrier matrix to which immobilizing ligands selected from -D-alanyl-D-alanine or -X-D-alanyl-D-alanine, wherein X is an amino acid radical, has been attached; (2) thereby, selectively forming an affinity sorption complex between the antibiotic and the immobilizing ligand; (3) washing the impurities from the matrix and complex attached thereto; and (4) dissociating the complex between the antibiotic and the immobilizing ligand to recover said purified antibiotic.

2. A process according to claim 1 wherein the antibiotic is selected from the group consisting of vancomycin, ristocetin, actinoidin, avoparcin, actaplanin, teichomycin A$_2$, LL-AM-374, A 477, OA 7653, A35512B, AAD 216 complex and the individual factors of said antibiotics.

3. A process according to claim 2 wherein the antibiotic is vancomycin.

4. A process according to claim 2 wherein the antibiotic is ristocetin.

5. A process according to claim 2 wherein the antibiotic is AAD 216 complex.

6. A process according to claim 2 wherein the antibiotic is avoparcin.

7. A process according to claim 2 wherein the antibiotic is teichomycin A$_2$.

8. A process according to claim 2 wherein the antibiotic is A35512B.

9. A process according to claim 1 wherein the dissociation of the sorption complex is accomplished by employing a basic buffer solution and a polar organic solvent.

10. A process according to claim 9 wherein the basic buffer solution is selected from the group consisting of 0.4 M sodium bicarbonate at pH 9.5, 0.5M triethylammonium carbonate at pH 9, 0.25M sodium bicarbonate at pH 9 and 0.25M sodium bicarbonate at pH 9.5.

11. A process according to claim 9 wherein the polar organic solvent is acetonitrile.

12. A process according to claim 1 wherein tne impure solution is a fermentation broth.

13. A process according to claim 1 wherein the immobilizing ligand is -D-alanyl-D-alanine.

14. A process according to claim 1 wherein the immobilizing ligand is selected from the group consisting of α-N-acetyl-L-lysyl-D-alanyl-D-alanine, ε-N-acetyl-L-lysyl-D-alanyl-D-alanine, glycyl-D-alanyl-D-alanine, L-alanyl-D-alanyl-D-alanine, L-ornithyl-D-alanyl-D-alanine, L-tryrosyl-D-alanyl-D-alanine and D-alanyl-D-alanyl-D-alanine.

15. A process according to claim 14 wherein the immobilizing ligand is α-N-acetyl-L-lysyl-D-alanyl-D-alanine.

16. A process according to claim 1 wherein the solid matrix support is selected from the group consisting of agarose, dextran, cellulose, polystyrene, polyacrylamide, silica, controlled pore glass, nylon, acrylic copolymers and polyesters.

17. A process according to claim 16 wherein the solid matrix support is selected from the group consisting of agarose, Sepharose and acrylic copolymers.

18. A process according to claim 17 wherein the solid matrix support contains spacer arms.

19. A process according to claim 18 wherein the solid matrix support is Affi-Gel ® 10.

* * * * *